United States Patent [19]

Zhuk et al.

[11] Patent Number: 4,916,225
[45] Date of Patent: Apr. 10, 1990

[54] 9-SUBSTITUTED GUANINES

[75] Inventors: Regina A. Zhuk; Marger J. Lidak, both of Riga; Marina A. Madre, Ogre; Veniamin I. Votyakov, Minsk; Olga T. Andreeva, Minsk; Evgeny I. Boreko, Minsk; Ljudmila V. Korobchenko, Minsk; Vyacheslav A. Rusyaev, Minsk; Olga I. Starkova, Minsk, all of U.S.S.R.

[73] Assignees: Institut Organicheskogo Sinteza Akademii nauk Latviiskoi SSR; Belorussky Nauchno-Issledovatelsky Institute Epidemiologii i Mikrobiologii

[21] Appl. No.: 242,191
[22] PCT Filed: Nov. 23, 1987
[86] PCT No.: PCT/SU87/00135
§ 371 Date: Jul. 14, 1988
§ 102(e) Date: Jul. 14, 1988
[87] PCT Pub. No.: WO88/03923
PCT Pub. Date: Jun. 2, 1988

[30] Foreign Application Priority Data
Nov. 25, 1986 [SU] U.S.S.R. .................. 4152348

[51] Int. Cl.$^4$ .................................... C07D 473/18
[52] U.S. Cl. ................................................ 544/276
[58] Field of Search .......................... 544/276

[56] References Cited
U.S. PATENT DOCUMENTS

| | | | |
|---|---|---|---|
| 3,228,937 | 1/1966 | Adcock | 544/277 |
| 3,903,169 | 9/1975 | Bader et al. | 568/314 X |
| 4,199,574 | 4/1980 | Schaeffer | 544/277 X |
| 4,241,063 | 12/1980 | Naito et al. | 544/277 X |
| 4,507,305 | 3/1985 | Verheyden | 514/262 |
| 4,612,314 | 9/1986 | Verheyden | 544/261 |
| 4,701,526 | 10/1987 | Kobe et al. | 544/251 |
| 4,748,176 | 5/1988 | Ishii et al. | 514/262 |
| 4,826,981 | 5/1989 | Kobe et al. | 544/276 |

FOREIGN PATENT DOCUMENTS

| | | | |
|---|---|---|---|
| 0103551 | 3/1984 | European Pat. Off. | |
| 2088366 | 6/1982 | United Kingdom | 514/261 |
| 2122197A | 1/1984 | United Kingdom | |
| 2122198A | 1/1984 | United Kingdom | |

OTHER PUBLICATIONS

McOmie, "Protective Groups in Organic Chemistry", Plenum Press, London & New York (1973), pp. 104–106.
Greene, "Protective Groups in Organic Synthesis", John Wiley & Sons, New York, (1981), p. 24.

Primary Examiner—Mukund J. Shah
Assistant Examiner—Diana G. Rivers
Attorney, Agent, or Firm—Ladas & Parry

[57] ABSTRACT

Novel compounds, 9-substituted guanines, with the following general formula

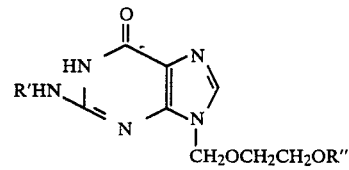

where
R' is acetyl;
R" is 2-tetrahydrofuryl or 2-tetrahydropyranyl.
The proposed compounds have antiviral activity.

1 Claim, No Drawings

9-SUBSTITUTED GUANINES

FIELD OF THE ART

The present invention relates to organic chemistry and more particularly it relates to novel compounds, 9-substituted guanines. Said compounds have antiviral activity.

PRIOR ART

Known in the prior art are various compounds having antiviral properties, e.g. 9-[2-hydroxyethoxymethyl]-guanine with the formula

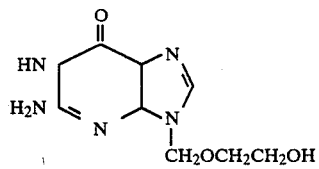

which is the active principle of the medicinal preparation acyclovir produced by Welcome (DE, A, 2539963).

The preparation acyclovir as an efficacious antiviral preparation of the second generation acting on the virus of herpes simplex HSV-1 and HSV-2, and also on the virus of herpes zoster and other viruses of man and animal.

The preparation is however sparingly soluble in water (2 mg/ml) and is therefore hephrotoxic with oral administration.

When given intravenously, its infusion is prolonged (2 h). Intramuscular administration of acyclovir is infeasible because of its low solubility; if the preparation penetrates occasionally into the surrounding tissues during intravenous injections, the tissues become affected with necrosis due to the high alkaline reaction of the injection solution (pH 11.0).

DISCLOSURE OF THE INVENTION

The proposed compounds are entirely new and have not been described in the literature.

The object of the invention is to provide new compounds with antiviral activity and higher solubility in water and lipophilic substances of the body.

Said object has been accomplished by providing, according to the invention, new compounds, 9-substituted guanines, with the general formula

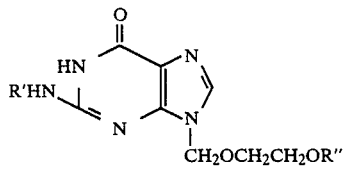

where
R' is acetyl or hydrogen, and
R'' is 2-tetrahydrofuryl or 2-tetrahydropyranyl.

The proposed compounds are crystalline substances, the structure of which has been proved by the complex of the physicochemical properties given in Tables 1, 2.

TABLE 1

Physicochemical properties of the proposed compounds

| Compound | M.p., °C. | $R_f$ in system chloroform: Methyl alcohol (10:2) | Found, in % C | H | N |
|---|---|---|---|---|---|
| 9-[2-(2-tetrahydrofuryloxy)ethoxymethyl]-$N^2$-acetylguanine | 162–163 | 0.63 | 49.6 | 5.6 | 20.7 |
| 9-[2-(2-tetrahydrofuryloxy)ethoxymethyl]guanine | 192–194 | 0.39 | 46.2 | 6.1 | 22.3 |
| 9-[2-(2-tetrahydropyranyloxy)ethoxymethyl]-$N^2$-acetylguanine | 135–136.5 | 0.66 | 51.1 | 6.0 | 19.7 |
| 1 | 2 | 3 | 4 | 5 | 6 |
| 9-[2-(2-tetrahydropyranyloxy)ethoxymethyl]guanine | 202–204 | 0.44 | 50.3 | 6.3 | 22.4 |

| Formula | Calculated, in % C | H | N |
|---|---|---|---|
| 7 | 8 | 9 | 10 |
| $C_{14}H_{19}N_5O_5$ | 49.8 | 5.7 | 20.8 |
| $C_{12}H_{17}N_5O_4 \cdot H_2O$ | 46.0 | 6.1 | 22.4 |
| $C_{15}H_{21}N_5O_5$ | 51.3 | 6.0 | 19.9 |
| $C_{13}H_{19}N_5O_4$ | 50.5 | 6.2 | 2.6 |

TABLE 2

Spectra of 9-substituted guanines

| Compound | U-V spectrum 0.01 M $H_3BO_3$ $\lambda_{max}$ ($\epsilon \times 10^{-3}$) in nm | PMR spectrum in dimethyl sulphoxide-$d_6$ (standard tetramethylsilan), δ m.d. |
|---|---|---|
| 9-[2-(2-tetrahydrofuryloxy)ethoxymethyl]-$N^2$-acetylguanine | 260(15.2)–274(11.1) | 12.01, 11.72(NH); 8.10($H_8$); 5.46(NCH$_2$); 5.02(CH); 3.60, 1.76 (CH$_2$); 2.18(CH$_3$) |
| 9-[2-(2-tetrahydrofuryloxy)ethoxymethyl]guanine | 253(10.4) 270(7.5) | 10.59(NH; 7.80($H_8$) 6.48(NH$_2$); 5.33(NCH$_2$); 5.03(CH); 3.36, 1.76(CH$_2$) |
| 9-[2-(2-tetrahydropyranyloxy)ethoxymethyl]-$N^2$-acetylguanine | 260(14.9) 276(10.7) | 11.99; 11.74(NH); 8.10($H_8$); 5.47(NCH$_2$); 4.49(CH); 3.61, 1.46 (CH$_2$); 2.18(CH$_3$) |
| 9-[2-(2-tetrahydropyranyloxy)ethoxymethyl]guanine | 253(10.5) 270(7.4) | 10.57(NH); 7.79($H_8$) 6.47(NH$_2$); 5.34(NCH$_2$); 5.11(CH); 3.62, 1.47(CH$_2$) |

MODE OF CARRYING OUT THE INVENTION

The antiviral activity of the proposed compounds was tested on animals and this activity was compared with that of acyclovir. The compounds were tested on mongrel albino mice with experimental herpetic encephalitis. The mice weighed 8-10 g. They were infected with the virus of herpes simplex type I. The mice were infected by two methods: intraabdominally with a dose 100 times exceeding LD$_{50}$, and intracerebrally in a dose of 10-30 LD$_{50}$. The substances were administered as aqueous solutions or suspensions with Tween 80 by two methods: intravenously and per os. The following scheme was followed: the first administration was in 3 hours after infection with the virus; then once a day the preparation was administered intravenously from the second to the seventh day. The daily dose for peroral administration was divided into two equal portions. The daily doses were from 0.01 to 200 mg/kg. The preparation for oral administration was dissolved in 0.1 ml of distilled water and for intravenous administration in 0.2 ml of distilled water.

Control mice were given the corresponding volume of an isotonic sodium chloride solution.

The efficacy of the compounds was estimated by decreasing mortality rate in the group of animals that were given the proposed compound and acyclovir. The death rate in these animals was compared with the mortality rate among the control animals. The results of the tests are given in Tables 3 and 4.

It can be seen from Table 3 that 9-[2-(2-tetrahydrofurylooxy)ethoxymethyl]-$N^2$-acetylguanine decreases death rate of mice with both intravenous and peroral administration of the preparation. Efficacy of the preparation is the same with both ways of administration. This can probably be explained by the fact that, the daily dose being the same, the oral dose was given by two intakes while the intraveous injection was given once a day. Two-fold administration of the compound within 24 hours increased the efficacy of the oral therapy and its efficacy approached that of intravenous therapy. The Table also shows that the efficacy of the proposed compound (maximum decrease in the mortality by 75 percent) is higher than that of acyclovir (decrease by 65.9 percent). The efficacy of 9-[2-(2-tetrahydrofuryloxy)ethoxymethyl]-guanine in similar experiments was 63 percent, of 9-[2-(2-tetrahydropyranyloxy)ethoxymethyl] guanine it was about 58 percent, and of 9-[2-(2-tetrahydropyranyloxy)ethoxymethyl]-$N^2$-acetylguanine, of the order of 15 percent.

The activity of 9[-2(2-tetrahydrofuryloxy)ethoxymethyl]-$N^2$-acetylguanine has also been studies on mice infected with the virus of herpes simplex intracerebrally, i.e. by direct administration of the herpesvirus into the brain. The dose of the virus was 10–30 times higher than $LD_{50}$ (the result of the tests are given in Table 4). The compounds were administered intravenously and per os according to the scheme described in the previous experiment.

It can be seen from Table 4 that the proposed compound has the antiviral effect within a wider range of doses.

With the oral administration of the compound, the maximum effect (lethality decreased by 56.3 percent compared with controls) was observed with daily doses of 100 and 200 mg/kg Acyclovir given in a daily dose of 100 mg/kg decreased lethality by 33.3 percent, and in a dose of 200 mg/kg only by 26.2 percent. The efficacy of both compounds was about the same with low doses (from 0.1 to 10 mg/kg).

When the proposed preparation was given intravenously in a dose of 10 mg/kg, the lethality decreased by 55.8 percent, which corresponds to the effect of accyclovir given in the same dose. But it is impossible to increase the dose of acycloriv without subsequent change in the pH of the solution due the limited solubility of the preparation. If however 9-[2-(2-tetrahydrofuryloxy)ethoxymethyl)]-$N^2$-acetylguanine is used, its dose can be increased to 100 mg/kg. The mortality rate as a result decreases by 66.5 percent. The range of the pharmacological effect of the proposed preparation is thus 10 times as high as of the known preparation acyclovir.

TABLE 3

Decreasing mortality of mice with herpetic encephalitis infected by intra-abdominal injection of herpes simplex virus type I and treated with 9-[2-(2-tetrahydrofuryloxy)ethoxymethyl]-$N^2$-acetylguanine and acyclovir

| | 9-[2-(2-tetrahydrofuryloxy)ethoxymethyl]-$N^2$-acetylguanine | | | Acyclovir | | |
|---|---|---|---|---|---|---|
| Dose, mg/kg | mortality, % ±m | decrease in mortality compared with control, % | P | mortality, % ±m | decrease in mortality compared with control, % | P |
| 1 | 2 | 3 | 4 | 5 | 6 | 7 |
| Oral administration | | | | | | |
| 200 | 25.0 | 60.0 | | 43.7 | 47.9 | |
| 100 | 18.7 | 66.3 | | 33.3 | 38.3 | |
| 10 | 10.0 | 75.0 | | 28.9 | 62.7 | |
| 1 | 20.0 | 65.0 | | 42.1 | 33.8 | <0.001 |
| 0.1 | 30.0 ± 15.3 | 55.0 | <0.01 | 57.8 ± 8.11 | 33.8 | >0.001 |
| 0.001 | 60.0 ± 16.3 | 25.0 | >0.05 | 83.3 ± 11.2 | 8.3 | >0.05 |
| Control | 85.7 ± 8.2 | | | 91.6 ± 4.0 | | |
| Intravenous injection | | | | | | |
| 100 | 11.1 | 69.8 | | ⊖ | — | |
| 10 | 5.5 | 75.4 | | 2.50 | 65.9 | |
| 1 | 12.5 | 68.4 | | 40.9 | 50.0 | |
| 0.1 | 22.2 ± 10.1 | 58.7 | <0.001 | 59.1 ± 10.7 | 31.8 | <0.05 |
| 0.01 | 60.0 ± 16.3 | 20.9 | >0.05 | 72.7 ± 9.7 | 18.2 | >0.05 |
| Control | 80.9 ± 8.8 | | | 90.9 ± 6.3 | | |

TABLE 4

Decrease in lethality of mice infected with herpes simplex virus intracerebrally and treated with 9-[2-(2-tetrahydrofuryloxy)ethoxymethyl]-$N^2$, acetylguanine and acyclovir

| | 9-[2-(2-tetrahydrofuryloxy)ethoxymethyl]-$N^2$-acetylguanine | | | Acyclovir | | |
|---|---|---|---|---|---|---|
| Dose, mg/kg | lethality, % ±m | decrease in lethality compared with control, % | P | lethality, % ±m | decrease in mortality compared with control, % | P |
| 1 | 2 | 3 | 4 | 5 | 6 | 7 |
| *Oral administration* | | | | | | |
| 200 | 25.0 | 56.3 | | 57.1 | 26.2 | |
| 100 | 25.0 | 56.3 | | 50.0 | 33.3 | |
| 10 | 37.5 | 43.8 | | 28.5 | 54.8 | |
| 1.0 | 50.0 | 31.3 | | 50.0 | 33.3 | |
| 0.1 | 50.0 ± 18.9 | 31.3 | <0.05 | 55.0 ± 11.4 | 28.3 | <0.03 |
| 0.01 | 75.0 ± 16.4 | 6.3 | >0.05 | 70.0 ± 10.5 | 13.3 | >0.05 |
| Control | 81.3 ± 10.1 | | | 83.3 ± 6.3 | | |
| *Intravenous injections* | | | | | | |
| 100 | 14.3 | 66.5 | | — | | |
| 10 | 25.0 | 55.8 | | 33.3 | 55.2 | |
| 1.0 | 37.5 | 43.5 | | 43.7 | 44.8 | |
| 0.1 | 41.6 ± 14.9 | 39.2 | | 64.3 ± 13.3 | 24.2 | >0.05 |
| 0.01 | 91.4 ± 8.3 | 0.0 | <0.02 | 78.5 ± 11.4 | 10.0 | >0.05 |
| Control | 90.8 ± 7.9 | | >0.05 | 88.5 ± 6.4 | | |

In experiments in vitro on a monolayer culture of primary fibroblasts of chick embryos infected with the virus of herpes simplex type I, the number of patches was counted. The decrease in the virus titre by more than 1.5 lg BFU/ml with 9-[2-(2-tetrahydrofuryloxy)ethoxymethyl]-$N^2$-acetylguanine, 9-[2-(2-tetrahydrofuryloxy)ethoxymethyl]guanine and 9-[2-(2-tetrahydropyranyloxy)ethomethyl]guanine was attained with concentration of 100 μg/ml, while with 9-[2-(2-tetrahydropyranyloxy)ethoxymethyl]-$N^2$-acetylguanine, this was attained with the concentration of 400 μg/ml. These concentrations are much higher than the minimum effective concentration of acyclovir. Since the experiments in vivo demonstrated the high antiviral activity of the proposed compounds, it can be suggested that they are activated in the bodily media, i.e. they act as transport forms as they convert into active compounds in the body. This probably explains the lower toxicity of the compounds compared with that of acyclovir.

The $LD_{50}$ of 9-[2-(2-tetrahydrofuryloxy)ethoxymethyl]-$N^2$-acetylguanine with a single intraperitoneal administration to mice is 3300 mg/kg, of 9-[2-(2-tetrahydropyranyloxy)ethoxymethly]guanine it is above 2000 mg/kg, while of acyclovir it is 1800 mg/kg.

The solubility in water of the proposed compounds is better than that of acyclovir. 9-[2-(2-tetrahydrofuryloxy)ethoxymethyl]-$N^2$-acetylguanine is especially readily soluble: 120 mg/ml. This is 60 times higher than the solubility of acyclovir (2 mg/ml).

The solubility of 9-[2-(2-tetrahydropyranyloxy)ethoxymethyl]-$N^2$-acetylguanine is also about 100 mg/mo, while the solubility of 9-[2-(2-tetrahydrofuryloxy)ethoxymethyl]guanine and of 9-[2-(2-tetrahydropyranyloxy)ethoxymethyl]guanine is 2.5–3 mg/ml. Besides, the proposed compounds are more soluble than acyclovir in low-polar organic solvents. For example, the solubility of 9-[2-(2-tetrahydrofuryloxy)ethoxymethyl]-$N^2$-acetylguanine in chloroform is 10 mg/ml, while that of acyclovir is lower than 1 mg/ml. It can therefore be suggested that 9-[2-(2-tetrahydrofuryloxy)ethoxymethyl]-$N^2$-acetylguanine better penetrates the lipophilic substances of the body, including the ganglia of the sensory nerves, where the viruses are accumulated during the latent period of the disease.

The proposed compounds are stable in neutral aqueous solutions (pH about 7.4), but are hydrolyzed in an acid medium at pH below 5.

The experimental findings indicate the following advantages of the proposed compounds over the known preparation acyclovir:

(a) much higher solubility (60 times as high) in water, which makes it possible to use the solutions of 9-[2-(2-tetrahydrofuryloxy)ethoxymethyl]-$N^2$-acetylguanine for intravenous and intramuscular injections;

(b) lower nephrotoxicity, and hence possible administration of the preparation in large doses (10 times as large), which decreases lethality from herpetic encephalitis in mice by 66.5 percent with the intracerebral infection with the virus and intravenous injections of the proposed compound (against 55 percent reduction obtainable with acyclovir);

(c) higher solubility in low-polar organic solvents (in which acyclovir is insoluble), which promotes penetration of the preparation into the ganglia of the sensory nerves where the virus is accumulated during the latent period of the disease.

The proposed compounds can be obtained by the following procedure.

A flask provided with a stirrer is loaded with 9-(2-acetoxyethoxymethyl)-$N^2$-acetylguanine and water is added. The obtained suspension is stirred with cooling to 0° C. to 5° C., and a precooled solution of sodium hydroxide is added. The flask contents are mixed at this temperature for 60 minutes and neutralized with acetic acid to pH 6–7. The resultant solution is kept at a temperature from 0° to −5° C. for 24 hours. The precipitated 9-(2-hydroxyethoxymethyl)-$N^2$-acetylguanine is separated on a filter, washed and dried.

The obtained 9-(2-hydroxyethoxymethyl)-$N^2$-acetylguanine is dissolved in dimethyl formamide at a temperature of 50°–60° C. The solution is cooled to a temperature from 0° to −5° C. and saturated with hydrogen chloride at this temperature. Then, 2,3-dihydrofuran or 2,3-dihydropyran is added with stirring. The reaction mixture is stirred for 2 hours at a temperature from 0° to −5° C., and then neutralized with triethylamine. The precipitated triethylamine hydrochloride is separated on a filter, the filtrate is evaporated in vacuum, and the residue is recrystallized from ethyl acetate and then from ethyl alcohol. The resultant product is 9-[2-(2-tetrahydrofuryloxy)ethoxymethyl]-N²-acetylguanine. If 2,3-dihydropyran is used instead of 2,3-dihydrofuran, the resultant product is 9-[2-(2-tetrahydropyranyloxy)ethoxymethyl]-N²-acetylguanine.

An aqueous solution of methylamine is added to the obtained 9-[2-(2-tetrahydrofuryloxy)ethoxymethyl]-N²-acethylguanine, the mixture is stirred for 2 hours at room temperature, and then evaporated in vacuum. The residue is recrystallized from an aqueous solution of ethyl alcohol.

The resultant product is 9-[2-(2-tetrahydrofuryloxy)ethoxymethyl]guanine.

If 9-[2-(2-tetrahydropyranyloxy ethoxymethyl]-N²-acetyle guanine is treated with an aqueous solution of methylamine, 9-[2-(2-tetrahydropyranyloxy)ethoxymethyl]guanine is obtained.

For a better understanding of the invention, the following examples of its practical embodiment are given by way of illustration.

EXAMPLE 1

A flask provided with a stirrer is loaded with 3.0 g (97 mmole) of 9-(2-acetoxymethyl)-N²-acetylguanine and 60 ml of water. The formed suspension is cooled to a temperature of 0° C. and 60 ml of a precooled (to 0° C.) 2N solution of NaOH are added with stirring. The reaction mixture is stirred for 60 minutes at a temperature between 0° and −5° C. and then neutralized with acetic acid to pH 6–7. The mixture is cooled for 24 hours and the precipitated substance is separated on a filter, washed with small quantity of cold water, and dried. The yield of 9-(2-hydroxyethoxymethyl)-N²-acetylguanine is 2.18 g (84%). The melting point of the product is 212°–214° C., $R_f$=0.21 (in the system of chloroform and methyl alcohol taken in the ratio of 10:2).

1.20 g (4.5 mmole) of 9-(2-hydroxyethoxymethyl)-N²-acetylguanine prepared as described above are placed in a flask provided with a stirrer and dissolved in 40 ml of dimethyl formamide at a temperature between 50° and 60° C. The resultant solution is cooled to a temperature between 0° and −5° C., and saturated with dry hydrogen chloride at this temperature. Next, 4 ml of 2,3-dihydrofuran are added to the reaction mixture with stirring and cooling to 0° C. The solution is stirred at a temperature between 0° and −5° C. for 3 hours, and then excess hydrogen chloride is neutralized with triethylamine.

The precipitated triethylamine hydrochloride is separated on a filter, washed with a small quantity of dimethyl formamide. The filtrate is evaporated in vacuum, and the residue is recrystallized from dry ethyl acetate and then from ethyl alcohol. The yield of 9-[2-(2-tetrahydrofuryloxy)ethoxymethyl]-N²-acetylguanine is 1.26 g (82.9%).

The physicochemical properties, that prove the structure of the compound, are given in Tables 1 and 2.

EXAMPLE 2

A flask provided with a stirrer is loaded with 1.18 g (3.5 mmole) of 9-[2-(2-tetrahydrofuryloxy)ethoxymethyl]-N²-acetylguanine obtained as described in Example 1. 20 ml of a 25 percent aqueous solution of methylamine are added and the reaction mixture is stirred at room temperature for 2 hours. The mixture is evaporated in vacuum at a temperature not above 30° C., the dry residue is recrystallized two times from an aqueous solution of ethyl alcohol. The yield of 9-[2-(2-tetrahydrofuryloxy)ethoxymethyl]-guanine is 0.87 g (84 percent).

EXAMPLE 3

A flask provided with a stirrer is loaded with 1.20 g (4.5 mmole) of 9-(2-hydroxyethoxymethyl)-N²-acetylguanine obtained as described in Example 2, and 40 ml of dimethyl formamide are added. The components are heated at 50°–60° C. to complete dissolution of the precipitate. The obtained solution is cooled to a temperature between 0° and −5° C. and saturated at this temperature with dry hydrogen chloride. Next, 4 ml of 2,3-dihydropyran are added gradually to the reaction mixture with stirring and cooling to 0° C. The solution is stirred for 3 hours at a temperature of 0°, and then excess hydrogen chloride is neutralized with triethylamine. The precipitated triethylamine hydrochloride is separated on a filter, and the filtrate is evaporated in vacuum. The residue is recrystallized from dry ethyl acetate and then from ethyl alcohol. The yield of 9-[2-(2-tetrahydropyranyloxy)ethoxymethyl]-N²-acetylguanine is 0.89 g (56.5 percent).

EXAMPLE 4

A flask provided with a stirrer is loaded with 1.23 g (3.5 mmole) of 9-[2-(2-tetrahydropyranyloxy)ethoxymethyl]-N²-acetylguanine obtained as described in Example 3 and 20 ml of a 25 percent aqueous solution of methylamine are added. The reaction mixture is stirred at room temperature for 2 hours and evaporated in vacuum at a temperature not above 30° C. The dray residue is recrystallized from an aqueous soluton of ethyl alcohol to give 0.86 g (80 percent) of 9-[2-(2-tetrahydropyranyloxy)ethoxymethyl]guanine.

The physicochemical properties of the compounds prepared in Examples 1 through 4, that prove their structure, are given in Tables 1 and 2.

INDUSTRIAL APPLICABILITY

The proposed compounds can be used in medicine.
What we claim is:
1. 9-substituted guanines of the formula

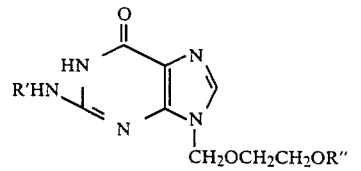

wherein R' is acetyl and R" is 2-tetrahydrofuryl or 2-tetrahydropyranyl.

* * * * *